US005753248A

United States Patent [19]
Bott et al.

[11] Patent Number: 5,753,248
[45] Date of Patent: May 19, 1998

[54] AMPHIPATHIC GRAFT COPOLYMER PESTICIDE FORMULATION COMPOSITIONS AND METHODS OF THEIR USE

[75] Inventors: Craig J. Bott, Clare; Dale M. Pickelman, Auburn; Ritchie A. Wessling, Midland, all of Mich.

[73] Assignee: The Dow Chemical Company, Midland, Mich.

[21] Appl. No.: 560,233

[22] Filed: Nov. 21, 1995

Related U.S. Application Data

[63] Continuation-in-part of Ser. No. 265,354, Jun. 24, 1994, abandoned, which is a continuation-in-part of Ser. No. 87,834, Jul. 2, 1993, abandoned.

[51] Int. Cl.[6] .................... C08F 2/04; A01N 25/04
[52] U.S. Cl. ........................ 424/405; 514/772.4
[58] Field of Search .............. 424/78.08, 70.16, 424/70.15, 405

[56] References Cited

U.S. PATENT DOCUMENTS

| | | | |
|---|---|---|---|
| 3,400,093 | 9/1968 | Feinberg | 260/29.6 |
| 3,660,537 | 5/1972 | Fryd et al. | 526/318 |
| 4,303,642 | 12/1981 | Kangas | 424/78 |
| 4,337,185 | 6/1982 | Wessling et al. | 524/458 |
| 4,427,819 | 1/1984 | Wessling et al. | 524/458 |
| 4,512,969 | 4/1985 | Chen | 424/81 |
| 5,089,259 | 2/1992 | Wessling et al. | 424/497 |
| 5,188,824 | 2/1993 | Wessling et al. | 424/78.1 |

FOREIGN PATENT DOCUMENTS

| | | |
|---|---|---|
| 0244145 | 4/1987 | European Pat. Off. . |
| 0357149 | 8/1989 | European Pat. Off. . |

OTHER PUBLICATIONS

Rogiers and Bognolo, Novel Trends in Dispersants, Aug. 10–15, 1986.
Yoshiki Chujo et al., Polymer Journal, vol. 17, No. 1, pp. 133–141 (1985).
Kazuhiko Ishihara et al., Journal of Polymer Science, vol. 32, 15 Apr. 1994, pp. 859–867.

*Primary Examiner*—Peter F. Kulkosky
*Attorney, Agent, or Firm*—S. Preston Jones; James M. Pelton

[57] ABSTRACT

The present invention further provides a substantially non-aqueous agricultural pesticide concentrate formulation of a non-ionic surfactant and a amphipathic graft copolymer composition in admixture with a water-insoluble organic agricultural pesticide which concentrate formulation can be easily diluted with water to form non-settling, freeze-thaw stable formulations.

The present invention further provides methods for the use of water-diluted agricultural pesticide concentrate formulations of the above non-ionic surfactant concentrate formulations in the kill and control of agricultural pest.

18 Claims, No Drawings

5,753,248

AMPHIPATHIC GRAFT COPOLYMER PESTICIDE FORMULATION COMPOSITIONS AND METHODS OF THEIR USE

CROSS-REFERENCE TO RELATED APPLICATIONS

This application is a continuation-in-part of application Ser. No. 08/265,354, filed Jun. 24, 1994, abandoned which is a continuation-in-part of application Ser. No. 08/087,834, filed Jul. 02, 1993, now abandoned.

FIELD OF THE INVENTION

This application relates to compositions containing amphipathic graft copolymers comprised of a hydrophobic backbone polymer to which is "in-chain" grafted at least one hydrophilic monomer, the use of said compositions in the kill and control of various agricultural pests and the preparation of said compositions.

In addition, the present invention provides a method for the use of water diluted formulations of the above dilutable substantially non-aqueous compositions, in the kill and control of various agricultural pests. The present invention also provides a method for the kill and control of agricultural pests in their growth environments which comprises contacting said pests or their environments with a pesticidally effective amount of the above water diluted formulation.

BACKGROUND OF THE INVENTION

As shown in U.S. Pat. No. 3,400,093, known methods for incorporating water-insoluble organic pesticides into water-based systems have been unsatisfactory in that the pesticides tend to settle out and do not remain uniformly dispersed in said systems. The patent further discloses a solution to that problem by employing emulsion polymerization of vinyl-type monomers in the presence of the pesticide. However, certain pesticides, such as chlorpyrifos and chlorpyrifos-methyl, tend to hydrolyze if heated to polymerization temperatures for extended periods of time and thus can not be used in this polymerized form. In addition, the presence of a pesticide in a monomer influences the polymerization to some degree, e.g., the rate of polymerization, the conversion and/or the molecular weight of the polymer produced.

U.S. Pat. No. 4,303,642 teaches that the above problems may be overcome by adding the pesticide to a finished latex wherein the polymeric particles are in a size range of from 0.03 to 20 microns. An increase in pesticide efficiency is demonstrated, although optimum stability and transfer of the pesticide through soil is not obtained.

U.S. Pat. No. 4,512,969 discloses compositions containing loaded latex particles of from 0.02 to 0.2 micron in average diameter consisting essentially of loadable polymer particles. A hydrophobic insecticide, herbicide, miticide, hormone, vitamin, or enzyme is loaded into and distributed through the latex particles. The weight ratio of the hydrophobic compound to the loadable polymer particle is from 1:40 to 3:1.

U.S. Pat. No. 5,188,824 discloses the preparation of a water dilutable emulsion concentrate of a water-insoluble organic pesticide which comprises an admixture of a water-insoluble organic pesticide and a water-based structured particle latex composed of non-ionic particle cores to which is bound a stabilizing layer containing stabilizing pH independent ionic groups chemically bound at or near the surface of the polymer cores wherein the pesticide is present in a weight ratio of from about 1:50 to about 10:1 in terms of the pesticide to the particles of the structured particle latex.

U.S. Pat. No. 5,089,259 discloses the preparation and use of stable, aqueous emulsion formulations of water-insoluble organic pesticides which are formed from a mixture of (1) a water-insoluble organic pesticide, (2) a structured particle latex containing non-ionic particles to which is bound a layer containing stabilizing pH independent ionic groups chemically bound at or near the particle surface of the polymer particles, and (3) optionally a co-solvent and/or a co-surfactant for the pesticide. The formulations are more stable to coalescence and freeze-thaw conditions than emulsions stabilized with conventional latex particles containing carboxyl or sulfonate groups.

Rogiers and Bognolo, *Novel Trends in Dispersants*, a paper presented at the Sixth International Congress of Pesticide Chemistry, Ottawa, Canada, Aug. 10–15, 1986, reported on the stabilization of an Ethirincol suspension concentrate with a graft stabilizer of a polymethylmethacrylate-polymethacrylic acid backbone copolymer grafted with polyethylene oxide.

Soil pesticides are usually incorporated in the soil mechanically or are spread on the surface thereof to be leached into the soil by rainfall. In either case, the pesticide may not be able to function properly because it can become immobilized at the point of application. This will certainly be the case for large hydrophobic molecules and the problem can be compounded further if the carrier is itself a large hydrophobic particle.

In conventional formulations the surfactants are adsorbed on the particle surface and are in equilibrium with the aqueous phase and the surface of soil particles. Since the surface area is so large, the soil tends to act as an infinite sink of low surfactant concentration and much of the surfactant initially on the pesticide particle transfers to the soil, whereupon the pesticide particle either deposits on the soil or flocculates, thereby losing the ability to migrate through the soil.

The emulsion polymerization of hydrophobic monomers in the presence of an ionic pH independent hydrophilic reactive polymeric surfactant (RPS) to form a seed latex having a hydrophilic backbone polymer containing grafting sites to which is grafted a hydrophobic polymer is known and described in, for example, U.S. Pat. Nos. 4,337,185 and 4,427,819.

In one method of producing structured particle latexes from these seed polymers, additional quantities of vinyl monomers are then added and emulsion polymerized to cause the particle of the seed to grow in size and attain the desired charge density. However, for the seed latex to function as a stabilizing layer at the growing particle surface, the polymeric hydrophilic/grafted hydrophobic composition must be substantially uncrosslinked, i.e., must not be a microgel. This is accomplished by adjusting the initiator and chain transfer agent in both polymerization processes of the water-soluble RPS composition and during the growth step to form the structured particle latex.

Non-aqueous emulsifiable concentrate formulations of water-insoluble organic pesticides are prepared with these high charge aqueous polymer colloids and an oil phase containing the pesticide, a hydrophobic oil diluent for the pesticide can be used if necessary, a non-ionic surfactant, and if desired, a co-surfactant, as described in European Pat. Application EP 0 357 149 A2. Such concentrates are prepared from an aqueous dispersion of the graft copolymer and are either water or oil-based depending on the water content.

A water removal step is required when adequate polymer levels are incorporated to form dilutable emulsifiable concentrates (ECs). Aqueous dilutions from water-based and oil-based formulations result in oil-in-water emulsions having a particle size of ≧2,000 Angstroms (Å).

It is known that the solubility of random copolymers varies with the relative proportion of its components. However, the solubility of graft copolymers is often unusually high, especially if the two components have widely different polarities. The molecular structure of graft copolymers can influence its solubility behavior. The graft copolymers discussed in the following two references demonstrate the useful stabilization capabilities of water-insoluble organic materials emulsified in water.

Yoshiki Chujo et al. in *Polymer Journal*, Vol. 17, No. 1, pages 133–141 (1985) describe the preparation of "comb-like" amphipathic graft copolymers employing the macromonomer process technique and their solubilization behavior with a water-insoluble organic material. These "comb-like" grafts which are made by the macromonomer process are "end-chain" grafts, i.e. the type of grafts made by the macromonomer process are attached to the backbone at the terminus of the monomer to be grafted.

Two types of graft copolymers were prepared: case (1) the copolymer has a hydrophilic ionic backbone with hydrophobic poly,(methyl methacrylate) grafted branch segments and case (2) the copolymer has a hydrophobic poly(methyl methacrylate) backbone with hydrophilic ionic grafted segments. Both types are capable of solubilizing a water-insoluble organic material in a mixed acetone-water medium. The graft copolymer with the hydrophobic backbone and the hydrophilic ionic branches (case 2) produces more rigid micelles in a water rich medium than that of a (case 1) system. Case (1) type micelles have a large hydrophobic core with a thin stabilizing surface whereas case (2) micelles have the inverse situation: micelles with a small hydrophobic core with a large or thick stabilizing surface.

Kazuhiko Ishihara et al. in *Journal of Polymer Science*, "Part A:Polymer Chemistry," Vol. 32, 15 Apr. 1994, pages 859–867, describe water-soluble graft copolymers with phospholipid groups. As these copolymers are made employing the macromonomer process method, they would be "comb-like" grafts, i.e. "end-chain" grafts. The characterizations of these graft copolymers are specifically taught on page 862.

The AGRIMER™AL family of products (International Specialty Products, marketers of GAF Reg. TM products) are graft copolymers (alkylated adducts) of vinylpyrrolidone and alpha-olefins. These "comb-like" copolymers vary in HLB ranging from 4 to 20 depending on chain length of the alkyl group and the degree of alkylation. These low molecular weight copolymers range in solubility with water, alcohol, mineral oil, vegetable oil, and alkyl aromatics depending on polymer HLB. Further, these products are useful as antiflocculants for oil-based flowables and suspension concentrates and stabilizers for oil-in-water emulsions.

Composite resin particles each comprising a particulate crosslinked polymer to which a number of substantially linear, metal-containing polymer chains are chemically bonded are known and taught in EP 0 244 145. The particles have the properties of the metal element contained therein and are useful in the paint industry. These particles are also taught to have biological activity.

It is desirable to provide a substantially non-aqueous emulsifiable concentrate formulation that yields particles of less than about 5000 Å which are smaller than heretofore available so as to improve the stability and application efficacy of dilutable concentrates of water-insoluble materials, especially water-insoluble organic pesticides.

SUMMARY OF THE INVENTION

The present invention provides a dilutable substantially non-aqueous concentrate formulation containing less than 15 percent water which is non-settling and freeze-thaw stable which comprises an amphipathic graft copolymer having charge densities of 0.5 to 1.5 meq/gram polymer and which have molecular weights of between 3,000 and 250,000, comprised of a hydrophobic backbone polymer prepared from at least two ethylenically unsaturated hydrophobic monomers, at least one of which is a couplable monomer which contains grafting sites to which is grafted as "in chain" sidechains (as hereinafter discussed), an amphipathic copolymer prepared from at least one ethylenically unsaturated hydrophilic monomer containing pH independent ionic groups, a water-insoluble organic agricultural pesticide and a non-ionic surfactant, said formulation when diluted in water forms an oil-in-water emulsion wherein the particle sizes are 5000 Å or less. It is also within the scope of the present invention to make very stable oil-in-water emulsions wherein the particle sizes are less than 1500 Å.

In yet another embodiment, this invention provides a stable water dilutable substantially non-aqueous composition comprising (1) a water-insoluble organic pesticidal material, (2) an organic solvent for the water-insoluble organic agricultural pesticidal material, if needed, (3) a monomeric non-ionic surfactant, (4) an amphipathic graft copolymer having a number average molecular weight of between 3,000 and 250,000, comprising a hydrophobic backbone copolymer prepared from at least two ethylenically unsaturated hydrophobic monomers, at least one of which contains grafting sites to which is "in chain" grafted an amphipathic copolymer prepared from at least one ethylenically unsaturated hydrophilic monomer containing stabilizing pH independent ionic groups, (5) less than 10 percent water and (6) formulation additives from the group consisting of neutralents, color and odor-masking agents, freeze-thaw agents, thermal fluctuation agents and antifoam agents.

In another embodiment, this invention provides a stable water dilutable substantially non-aqueous composition comprising (1) a water-insoluble organic pesticidal material, (2) low vapor pressure inert plasticizers/oligomers or mixtures of low vapor pressure inert plasticizers/oligomers and high vapor pressure solvent (3) a monomeric non-ionic surfactant, (4) an amphipathic graft copolymer as set forth hereinabove, (5) less than 10 percent water and (6) formulation additives as set forth hereinabove. The formulations set forth herein are useful in treating situations where conservation tillage, reduced till or no-till practices are employed.

In addition, the present invention provides a method for the use of water diluted formulations of the above dilutable substantially non-aqueous compositions in the kill and control of various agricultural pests. The present invention also provides a method for the kill and control of agricultural pests in their growth environments which comprises contacting said pests or their environments with a pesticidally effective amount of the above water diluted formulation.

The present process provides product amphipathic graft copolymers having charge densities of 0.5 to 1.5 milliequivalents (meq)/gram polymer. The copolymer molecular weights are less than 250,000, preferably less than about 50,000, and most preferably less than about 35,000, and greater than about 3,000.

In addition, a method of packaging such dilutable substantially non-aqueous formulations containing a water-insoluble organic agricultural pesticide for safe and convenient handling is provided for. This method provides for producing formulations in a form which allows for ease in pesticide application by confining said dilutable substantially non-aqueous concentrate formulation within a bag wherein the container wall is a polymeric film which is soluble in an aqueous medium. When the bag is added to an aqueous medium in a tank, the bag dissolves and the concentrate formulation mixes to form a ready-to-use diluted formulation.

DETAILED DESCRIPTION OF THE INVENTION

The present invention provides a dilutable substantially non-aqueous concentrate formulation containing less than 15 percent water which is non-settling and freeze-thaw stable which comprises an amphipathic graft copolymer having charge densities of 0.5 to 1.5 meq/gram polymer and which have molecular weights of between 3,000 and 250,000, comprising a hydrophobic backbone polymer prepared from at least two ethylenically unsaturated hydrophobic monomers, said polymer containing grafting sites to which is "in-chain" grafted at least one ethylenically unsaturated hydrophilic monomer containing stabilizing pH independent ionic groups, a water-insoluble organic agricultural pesticide, a non-ionic surfactant and optional inert ingredients, said formulation when diluted in water forms an oil-in-water emulsion wherein the particle sizes are 5000 Å or less. It is also within the scope of the present invention to make very stable oil-in-water emulsions wherein the particle sizes are less than 1500 Å.

The amphipathic graft copolymers can be prepared employing a procedure which comprises starting the polymerization of at least two ethylenically unsaturated hydrophobic monomers, wherein at least one of the monomers is a couplable monomer, in a reaction medium and then starting the addition thereto of the ethylenically unsaturated hydrophilic monomers, including at least one anionic and/or cationic ionic monomer, or a post reactive non-ionic monomer that can be converted to a pH independent ionic derivative thereto, polymerizing said monomers and recovering the thus prepared amphipathic graft copolymer in a solution containing less than 15 percent by weight water.

It is important that the hydrophobic monomers are added to the polymerization medium first and the polymerization thereof initiated prior to the addition of the hydrophilic monomers. When using the reverse order of reactant addition in this process, i.e., making copolymers with a hydrophilic backbone and hydrophobic grafts, one obtains an unusable gel. This gel product, cannot be easily formulated, i.e., a non-homogeneous formulation occurs. Thus formulations made using the gel settle and are not freeze-thaw stable such as those of the instant invention.

The amphipathic graft copolymer compositions, can also be prepared by free-radical polymerizing in a first stage, a solution comprising at least two hydrophobic monomers including aliphatic, aromatic, and graftable types, in a medium of non-ionic surfactants and/or organic solvents which are compatible for solution polymerization and then copolymerizing in a two-step second stage, hydrophilic monomers, including at least one anionic and/or cationic ionic monomer, or a post reactive non-ionic monomer that can be converted to a pH independent ionic derivative, in the presence of said first stage polymerization product mixture and recovering the thus produced copolymer product solution containing less than 15 percent by weight water.

The reaction scheme can be represented as follows:

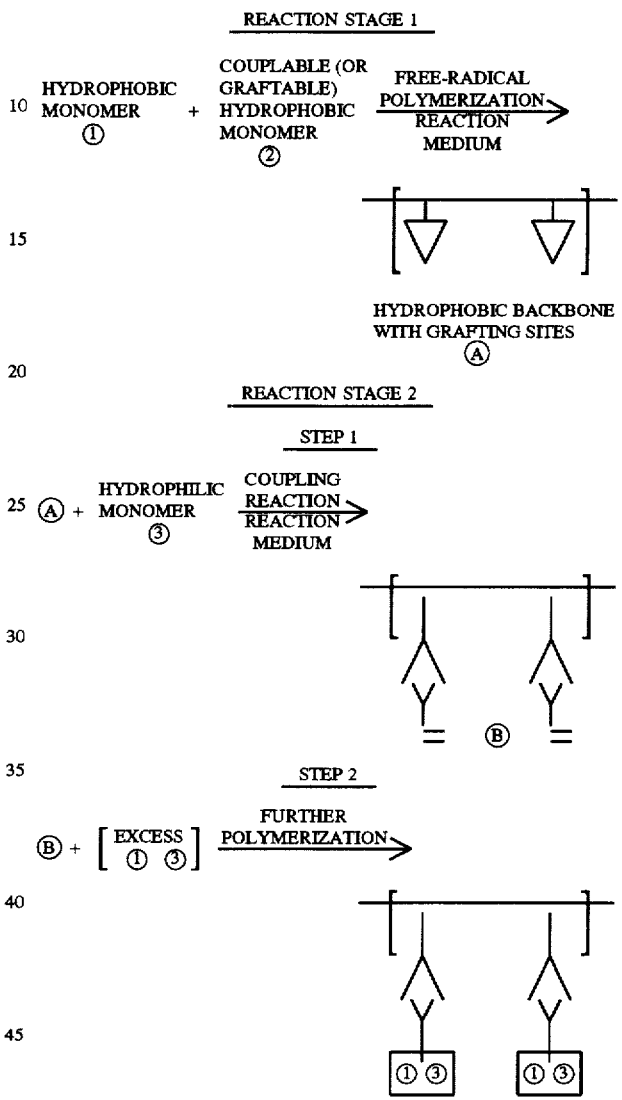

While the above reaction scheme depicts the presence of only one hydrophobic monomer (1), one couplable (graftable) hydrophobic monomer (2) and one hydrophilic monomer (3), the present invention provides for the use of more than one of each of said monomers. The choice of the specific monomers to employ depends on the specific type of amphipathic graft copolymer product desired. This invention also allows for the use of different monomers in REACTION STAGE 2. This can be accomplished by allowing polymerization in REACTION STAGE 1 to go essentially to completion prior to the STAGE 2 reaction. Different monomers can then be added for reaction in REACTION STAGE 2 to give products prepared from mixed monomers 1 or various combinations of monomers where different monomers 3 are added for reaction in STEP 2 of REACTION STAGE 2. Other such modifications are within the scope of those skilled in the art.

The above reaction scheme clearly shows and depicts the formation of "in-chain" grafts. In STEP 1 of REACTION STAGE 2, reaction product A is coupled with monomer 3 through a coupling reaction to form an intermediate reaction product B having pendant vinyl groups. This coupling is depicted by the two v groups shown being within one another. In STEP 2 of REACTION STAGE 2, the intermediate reaction product B free-radically copolymerizes with excess 1 from REACTION STAGE 1 and excess 3 from STEP 1 of REACTION STAGE 2. This free-radical copolymerization randomly incorporates the ethylenically unsaturated part of the intermediate B product statistically in the chain of the graft copolymer formed from the reaction of intermediate reaction product B and excess monomers 1 and 3. The resulting grafted segments will have 2n number of chain ends, resulting from the "in-chain" copolymerization, where n is the number of pendent ethylenic unsaturation sites on the reaction product B. This is in contrast with copolymers made by the macromonomer process which will only have n chain ends on the graft segment as a consequence of the exclusively terminal grafting nature of the macromonomer procedure.

The above reaction scheme is depicted hereinafter employing styrene and 2-ethylhexyl acrylate (2-EHA) as hydrophobic monomers, glycidyl methacrylate (GMA) as a couplable functional hydrophobic monomer and 2-acrylamido-2-methylpropane sulfonic acid (AMPS) as a hydrophilic monomer. The chemical formulas for these materials are as follows:

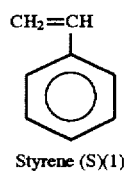

Styrene (S)(1)

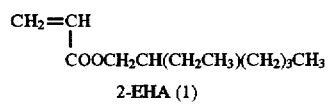

2-EHA (1)

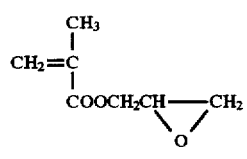

GMA (2)

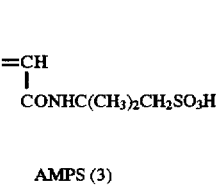

AMPS (3)

The reaction scheme employing the above listed chemicals is presented for illustration only as follows:

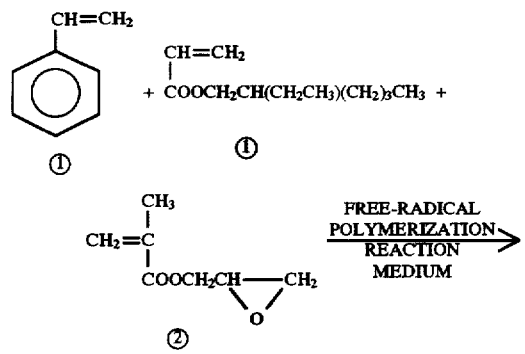

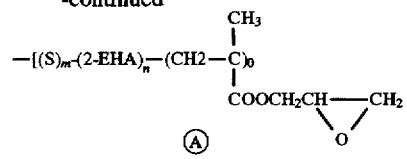

REACTION STAGE 2

STEP 1

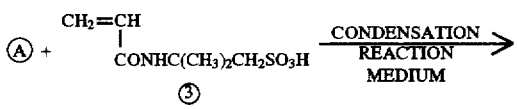

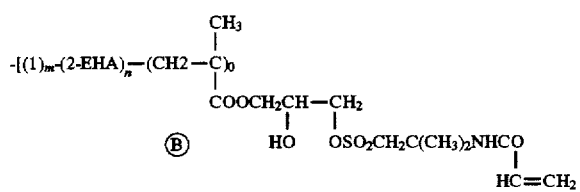

STEP 2

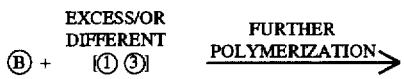

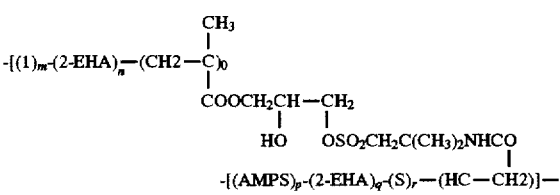

In the above reaction scheme, the terms "m", "n", "p", "q" and "r" are representations of random repeating units as understood by those skilled in this art.

In the present specification and claims, the term "amphipathic copolymer" is used to denote copolymers having both hydrophobic and hydrophilic components in the same molecule. The use of this term and its definition is taught by Irja Piirma in *Polymeric Surfactants*, Surfactant Science Series, Vol. 42, page 18, 1992.

In the present specification and claims, the term "hydrophobic" refers to those ethylenically unsaturated monomers which do not dissolve to any great degree in water, i.e. no more than about <1 percent.

In the present specification and claims, the term "hydrophilic" refers to those ethylenically unsaturated monomers which have a strong tendency to bind with water, absorb water or dissolve in water.

In the present specification and claims, the terms "stable", "freeze-thaw stable" or the like indicates that the formulation being discussed is not subject to phase separation and passes the hereinafter set forth freeze-thaw test.

In the present specification and claims, the term "thermal fluctuation" or the like indicates that the formulation being discussed is not subject to phase separation during storage under varying temperature conditions.

The free-radical polymerization reaction for preparing the amphipathic graft copolymers of the present invention is conducted by adding at least two hydrophobic monomers at least one of which is a graftable monomer and at least one hydrophilic monomer to a reaction medium at a temperature of from about 70° to about 110° C., or more, under an inert atmosphere of nitrogen. In this operation, the hydrophilic reactants are added to reaction mixture after partial polymerization of the hydrophobic monomers occurs, and the polymerization reaction continued to the completion of the reaction. The reaction is usually complete in a period of from about 2 to about 8 hours, or more.

The polymerization reaction employed for preparing the amphipathic graft copolymers of the present invention is preferably conducted in two stages employing conventional solution free-radical polymerization reaction conditions. In the first stage, the reaction is conducted at a temperature of from about 70° to about 110° C. under an inert atmosphere of nitrogen. The reaction is complete in a period of from about 2 to about 6 hours, or more. The products of the first stage are usually not separated and are used in the second stage without purification. The second stage is conducted at a temperature of from about 70° to about 110° C. and the reaction is also complete in a period of from about 2 to about 6 hours, or more.

As indicated hereinabove, during the second stage two different steps occur. In the first step, the copolymer product of the first stage is coupled with the hydrophilic monomer to form an intermediate product having pendant vinyl groups. This product then reacts in the second step with excess hydrophobic monomer present in the reaction medium and excess hydrophilic monomer present in the reaction medium and while undergoing free-radical copolymerization randomly incorporates statistically with the ethylenically unsaturated part of the intermediate product to produce "in chain" graft copolymers from the reaction of intermediate reaction product the excess hydrophobic and hydrophilic monomers.

This free-radical copolymerization randomly incorporates the ethylenically unsaturated part of the B product statistically in the chain of the graft copolymer formed from the reaction of reaction product B and excess monomers 1 and 3. The resulting grafted segments will have 2n number of chain ends, resulting from the "in-chain" copolymerization, where n is the number of pendent ethylenic unsaturation sites on the reaction product B. This is in contrast with copolymers made by the macromonomer process which will only have n chain ends on the graft segment as a consequence of the exclusively terminal grafting nature of the macromonomer procedure.

After the completion of the polymerization reaction, the reaction mixture is cooled and the amphipathic graft copolymer product thus produced can be used without purification or, if desired, the product can be purified to remove residual volatiles by conventional treatments such as steam and/or vacuum distillation.

The preferred procedure for making the hydrophobic/hydrophilic amphipathic graft copolymers of the present invention is to solution/free-radically polymerize at least two hydrophobic ethylenically unsaturated monomers including a graftable comonomer and then contacting the thus formed polymer with the hydrophilic monomers in a solvent and/or non-ionic surfactant medium containing a limited amount of water.

The hydrophobic monomer reactant and the hydrophilic monomer reactant are present in the reaction medium in the weight ratio of from about 1:1 to about 10:1 and preferably from about 3:1 to about 10:1 of the hydrophobic monomer to the hydrophilic monomer.

The hydrophobic ethylenically unsaturated monomers useful in this invention are suitably derived from any copolymerizable ethylenically unsaturated monomer, which, when in the form of an amorphous homopolymer, would have a solubility in water of less than 0.1 percent.

Representative hydrophobic monomers include: hydrocarbon monomers such as the styrene compounds, e.g., styrene, alpha methylstyrene, ring substituted methylstyrene, ring substituted ethylstyrene, ring substituted dimethylstyrene, ring substituted dimethylstyrene and t-butylstyrene; the conjugated dienes, e.g., butadiene, and isoprene; the hydrocarbon monomers which are modified to possess non-ionic substituents, e.g., hydroxystyrene, methoxystyrene and cyanostyrene; the unsaturated alcohol esters such as vinyl acetate and vinyl propionate; the unsaturated ketones, e.g., vinyl methyl ketone and methyl isopropenyl ketone; the unsaturated ethers, e.g., vinyl ethyl ether and vinyl methyl ether; and the non-ionic derivatives of ethylenically unsaturated carboxylic acids such as acrylic esters, e.g., methyl acrylate, ethyl acrylate, butyl acrylate, hexyl acrylate, 2-ethylhexyl acrylate and lauryl acrylate; methacrylic esters, e.g., methyl methacrylate, ethyl methacrylate, butyl methacrylate, hexyl methacrylate, 2-ethylhexyl methacrylate, and lauryl methacrylate; the maleic esters such as dimethyl maleate, diethyl maleate and dibutyl maleate; the fumaric esters, e.g., dimethyl fumarate, diethyl fumarate and dibutyl fumarate; and the itaconic esters, e.g., dimethyl itaconate, diethyl itaconate and dibutyl itaconate; and the nitriles, e.g., acrylonitrile and methacrylonitrile. The preferred hydrophobic monomers are styrene and 2-ethylhexyl acrylate.

Additionally, non-ionic monomers which form water-soluble homopolymers, e.g., acrylamide, methacrylamide, hydroxyethyl acrylate and hydroxyethyl methacrylate, may be mixed with a hydrophobic monomer in small amounts up to about 10 percent, based on the amount of hydrophobic monomer.

Minor amounts (less than 10 percent by weight) of a graftable reactive functional group which is either in the hydrophobic polymer backbone or pendant therefrom are present. As used herein, the term "graftable" as applied to the reactive group, means that the reactive group does not interfere with vinyl polymerization or react so rapidly in the presence of water that the group is not available for post reaction. The reactive functional group provides a crosslinking or grafting site for the second stage vinyl polymerization.

A wide variety of graftable reactive functional groups may be employed. Groups that undergo free-radical addition or chain transfer reactions may be used. This group includes ethylenic unsaturation both in the backbone or in the pendant groups. Groups that undergo condensation or coupling reactions are preferred. Epoxy groups, carboxy groups, hydroxy groups and sulfhydryl (—SH) groups are of this type. The reactive functional group may be part of the hydrophobic unit as, for example, a copolymerized butadiene unit, or it may be a substituent. The reactive group may be in the hydrophobic polymer, as made, or may be added by a subsequent "post-reaction". The preferred monomer to provide the graftable functional groups is glycidyl methacrylate.

The hydrophilic monomers useful in this invention include pH independent ionic monomers including positively and negatively charged species (e.g., sulfonate, sulfate, quaternary phosphonium groups, quaternary ammonium groups, pyridinium groups, sulfonium groups, isothiouronium groups and the like) to provide the ionic hydrophilic units. These monomers can be present in an amount from about 0.5 to about 1.5 meq/gram of polymer.

The above hydrophilic monomers may be defined as being any ethylenically unsaturated pH independent ionic monomeric unit (i.e., repeat unit in the polymer chain) which when in the form of a homopolymer is water-soluble. This includes: the sulfoalkylacrylates and methacrylate such as 3-acrylatopropanesulfonic acid, 2-methacrylato-2-methacrylatoethanesulfonic acid, 2-methacrylatopropanesulfonic acid, 2-sulfoethyl methacrylate, sodium vinylsulfonate and 2-hydroxy-3-sulfopropyl methacrylate; the acryl- and methacrylamidoalkylsulfonic acids and their salts such as 2-acrylamidopropanesulfonic acid, 2-acrylamidobutanesulfonic acid, 2-acrylamido-2-(4-tolyl) ethanesulfonic acid, 2-acrylamido-2-methylpropanesulfonic acid (AMPS), 2-methacrylamido-2-phenylethanesulfonic acid, 2-acrylamido-2-phenylpropanesulfonic acid, 3-acrylamido-2,3-dimethylbutanesulfonic acid and 3-acrylamido-2,4,4-trimethylpentanesulfonic acid; the styrene sulfonates such as sodium styrene sulfonate and 4-styrenesulfonic acid; the vinyl sulfonates such as vinylsulfonic acid; the vinyl-substituted quaternary ammonium salts such as N,N,N-trimethyl-N-methacryloxy-ethyl ammonium chloride, N,N,N-trimethyl-N-methacryloxy (2-hydroxypropyl) ammonium chloride, N-(3-sulfopropyl)-N-methacryloxy-ethyl-N, N-dimethyl ammonium betaine and the like; vinylbenzyldialkyl sulfonium salts such as dimethyl vinylbenzylsulfonium chloride and the like. The preferred pH independent ionic monomers contain sulfonate or quaternary ammonium groups.

Water may be added in minor amounts to aid in handling the pH independent monomer(s). The initiator and chain transfer agent levels employed during polymerization reaction can be adjusted to keep the molecular weight low, e.g., essentially gel free, so that the copolymer can function as a carrier for water-insoluble organic pesticide materials in a dilutable substantially non-aqueous formulation and also perform as a stabilizer when said formulation is diluted with water.

The initiators used in the polymerization process are of the type which produce free-radicals and conveniently are peroxygen compounds, for example: the organic hydroperoxides such as cumene hydroperoxide and t-butyl hydroperoxide; the organic peroxides such as benzoyl peroxide, acetyl peroxide, lauroyl peroxide, t-butyl peroctoate, t-butyl perbenzoate, diisopropyl peroxidicarbonate, peracetic acid and perbenzoic acid, sometimes activated by water-soluble reducing agents such as a ferrous compound, sodium bisulfite, sodium formaldehyde sulfoxylate or hydroxylamine hydrochloride and other free-radical producing materials such as VAZO™, azobisalkylnitrile initiators from DuPont. The peresters and azo compounds are preferred initiators. The initiators are present in an amount of from about 1.0 to about 5.0 weight percent based on the amount of the monomers present.

Most conventional chain transfer agents can be used in the process, with alkyl polyhalides and mercaptans being preferred. Examples are iodomethane, bromoform, carbon tetrachloride, carbon tetrabromide, bromoethane, alkyl mercaptans of from 1 to 12 carbon atoms, thiophenol, hydroxyalkyl mercaptans and carboxyalkyl mercaptans. The chain transfer agents are present in an amount of from about 0 to about 3.0 weight percent based on the amount of the monomers present.

The reaction medium useful in the process for preparing the copolymers of the present invention include those solvents which are compatible and defined by a solubility parameter range of about 8 to about 14 $(cal/cm^3)^{0.5}$. The solubility parameter value for various solvents is listed in H. Burrell, *Polymer Handbook*, second edition, (J. Brandrup and E. H. Immergut, editors) Wiley Interscience, New York, 1975, IV–337, Tables 1 and 2, pages 341–348. Representative solvents include, for example, butyrolactone, dioxane, dipropylene glycol methyl ether, methyl ethyl sulfone, methyl laurate, N-dodecyl pyrrolidone, N-methyl pyrrolidone, N-octyl pyrrolidone and tetrahydrofurfural alcohol. The solvents are present in the reaction medium in an amount of from 0 to about 500 weight percent based on the amounts of the monomers used.

The non-ionic surfactants useful in the process for preparing the copolymers of the present invention are those with a hydrophilic-lipophilic balance (HLB) range of 8 to 20, preferably 8 to 14. The HLB number value for various surfactants is listed by W. C. Griffin, in *Kirk-Othmer Encyclopedia of Chemical Technology*, 3rd ed. (M. Grayson, ed.) Vol. 8, Wiley-Interscience, New York, 1979, pages 900–930.

Typical non-ionic surfactants useful in the process for preparing the copolymers of the present invention are compounds formed by the reaction of an alkylene oxide, such as ethylene oxide, propylene oxide or butylene oxide with $C_6$–$C_{20}$ long chain fatty alcohols, $C_6$–$C_{20}$ long chain fatty acids, castor oil, $C_8$–$C_{12}$ alkylated phenols, $C_6$–$C_{20}$ long chain alkyl mercaptans, $C_6$–$C_{20}$ long chain alkyl primary amines, for example, cetylamine, the alkylene oxides being reacted in a ratio of such as 5 moles to 20 moles or higher such as up to 50 moles per mole of the co-reactant.

Similarly effective compounds are monoesters such as the reaction products of a polyethylene glycol with a long chain fatty acid, for example, glycerol monostearate, sorbitan trioleate and partial and complete esters of long chain carboxylic acids with polyglycol ethers of polyhydric alcohols. The preferred non-ionic surfactants are ethylene oxide adducts of alkylated phenols.

The non-ionic surfactants are present in an amount of from about 50 to about 500 weight percent based on the amount of the monomers present.

The term "long chain" as used in the present specification and claims defines an aliphatic group having from 6 to 20 carbon atoms or more.

Another approach to making the amphipathic graft copolymer compositions of the present invention is to prepare a hydrophobic interpolymer containing non-ionic functional units which can be later converted to ionic units.

The hydrophobic interpolymers are more readily prepared because of the compatibility of the components. Monomers and polymers being of similar polarity normally do not require the presence of a compatibilizing component. Illustrative of post reactions which can be carried out on functionally substituted polymers to yield ionic or reactive units are the following: displacement reactions on N,N-dimethylaminoethyl methacrylate units to yield quaternary ammonium groups; esterification of acids, acid chlorides or anhydrides to yield sulfoesters such as the reaction of methylacryloyl chloride units with isethionic acid to 2-sulfoethyl methacrylate, and the like.

Such post reactions also allow the preparation of copolymerized units which cannot be isolated in the monomeric stage or cannot be prepared in water. These units can be formed as follows:

Step (1) polymerizing, in a second stage vinyl polymerization, a mixture of ethylenically unsaturated non-ionic monomers wherein at least one of the monomers contains a reactive group (other than the polymerizing double bond) which reactive group does not interfere with the vinyl polymerization or react rapidly with the polymerization medium, then Step (2) adding to the solution from the above step (1), a co-reactant compound in sufficient amount to convert the functional group to a pH independent charge (i.e., positive or negative charge).

In Step (2), the substantially non-aqueous solution of Step (1) is converted to a dilutable amphipathic graft copolymer composition.

Any reaction parameters which promote the reaction between an added component, i.e., one having a molecular weight of less than 500, and the functional groups on the polymer chain to yield pH independent sites thereon, can be employed. Exemplary of said parameters are increased heat or pressure and changing the polarity of the reaction medium by addition of a polar solvent. The above parameters promote the reaction between the nucleophile and non-ionic alkylating agents to yield an organic cation as illustrated below:

$$RA + Z \rightarrow RZ+ A-$$

where Z is a nucleophile, RA is the alkylating agent and A is a leaving group. RZ+ is the derived onium cation and A— its anion formed from the leaving group. Either reactant can be a substituent on the polymer chain and its counterpart co-reactant is selected so as to yield a cationic amphipathic graft copolymer composition. It is, therefore, possible to make the same cationic product from these two different routes.

Non-ionic monomers which form copolymers with nucleophilic sites include the general classes of tertiary amines, aromatic heterocyclic amines (e.g., pyridines), phosphines and sulfides containing at least one polymerizable double bond as a substituent. Examples include vinyl pyridines, vinylbenzyl dialkyl-amines, dialkylaminoalkyl acrylates and methacrylates and alkylthioalkyl acrylates and methacrylates. The preferred non-ionic monomers with nucleophilic sites are dialkylaminoalkyl methacrylates.

Mixtures of polymers from Step (1) with the desired alkylating agent are allowed to react from ambient temperature to about 100° C., or higher if under pressure, to convert the nucleophilic sites to attached onium ions. As the reaction proceeds, the polymer becomes increasingly hydrophilic and eventually forms the desired amphipathic graft copolymer composition. After the reaction is complete, the reaction product can be recovered and used as is or it can be further purified by conventional treatments to remove unreacted alkylating agents.

The alkylating agents are selected to be highly reactive and volatile and must be at least slightly soluble. Preferred alkylating agents include alkyl bromides and iodides of 1 to 4 carbons, allyl and methallyl chlorides, benzyl chlorides and dimethyl sulfide.

Preferentially, the alkylating site may be placed on the polymer chain by using an active halogen-containing comonomer of the classes: vinyl aralkyl halides, haloalkyl butadienes, bromoalkyl acrylate and methacrylates and vinyl bromide. Preferred are vinylbenzyl chloride, chloromethylbutadiene and the bromoalkyl methacrylate esters. Polymers from (1), containing these alkylating sites in copolymerized form, are reacted with carbon-containing nucleophiles which are stable in, and can diffuse through, aqueous media having a hetero atom as the center of nucleophilicity wherein each covalent bond of said hetero atom is attached to a carbon atom.

The nucleophilic compounds which are used advantageously in the preparation of the dilutable amphipathic graft copolymer composition are represented by the following classes of compounds, sometimes called Lewis bases:

(a) monobasic aromatic nitrogen compounds;
(b) tetra (lower alkyl) thioureas;
(c) $R_1$-S-$R_2$, wherein $R_1$ and $R_2$ individually are lower alkyl, hydroxy lower alkyl or wherein $R_1$ and $R_2$ are combined as one alkylene radical having 2 to 5 carbon atoms;

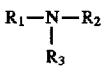

wherein $R_2$ and $R_3$ individually are lower alkyl or hydroxy lower alkyl, or are combined as one alkylene radical having 3 to 5 carbon atoms and $R_1$ is lower alkyl, aralkyl or aryl except when $R_2$ and $R_3$ together are an alkylene radical then $R_1$ is lower alkyl or hydroxy lower alkyl or hydroxy lower alkyl; and

wherein $R_1$, $R_2$ and $R_3$ individually are lower alkyl, hydroxy lower alkyl or aryl.

In the present specification, the term "lower alkyl" is used to define alkyl groups having from 1 to 4 carbon atoms such as methyl, ethyl, propyl, isopropyl, n-butyl and isobutyl.

Representative specific nucleophilic compounds are pyridine, quinoline, isoquinoline, tetramethyl thiourea, tetraethyl thiourea, hydroxyethylmethyl sulfide, hydroxyethylethyl sulfide, dimethyl sulfide, diethyl sulfide, di-n-propyl sulfide, methyl-n-propyl sulfide, methylbutyl sulfide, dibutyl sulfide, dihydroxyethyl sulfide, bis-hydroxybutyl sulfide, trimethylene sulfide, thiacyclohexane, tetrahydro-thiophene, N-methylpiperidine, N-ethylpyrrolidine, N-hydroxyethylpyrrolidine, trimethylphosphine, triethylphosphine, tri-n-butylphosphine, triphenylphosphine, trimethylamine, triethylamine, tri-n-propylamine, tri-isobutylamine, hydroxyethyldimethylamine, butyldimethylamine, trihydroxyethylamine, and N,N,N-dimethylphenethylamine.

The use of the nucleophilic component as a reactant is the preferred route because the monomer containing alkylating sites are less likely to interfere with vinyl polymerization and the co-reactant nucleophiles are more compatible and blend more readily into the reaction mixture. They are also easier to remove in a post-reactive cleanup and are less toxic than co-reactant alkylating agents.

Another general class of reactions suitable for the present process are the reactions of epoxides with nucleophiles and acids as shown below:

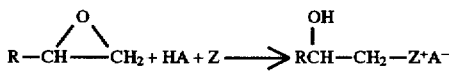

As described earlier, either the epoxide or the nucleophile may be attached to the polymer chain. Epoxide groups may be incorporated into the copolymer by, for example, copolymerization of an unsaturated epoxide such as glycidyl acrylate or methacrylate. Alternatively, the nucleophilic polymers described earlier can be reacted with a lower alkyl epoxide such as ethylene oxide, propylene oxide, epichlorohydrin, glycidyl ethers and the like. Suitable acids for either case include HCl, $H_2SO_4$ and lower carboxylic acids, and are typically selected on the basis of the anion desired.

The low water content non-ionic surfactant/amphipathic graft copolymer solution compositions of this invention are particularly useful as carriers for various water-insoluble organic agricultural pesticides in preparing dilutable substantially non-aqueous concentrate formulations.

The dilutable substantially non-aqueous concentrate formulations of the present invention can be employed to function in agricultural pesticidal use formulations including those which function as acaricides, algicides, antimicrobials, attractants, bactericides, fungicides, mulluscicides, repellants, rodenticides, herbicides and other plant growth controlling materials including insecticides, fungicides, nematicides and parasiticides as well as soil sterilants.

The agricultural pesticide containing dilutable substantially non-aqueous concentrate formulations of the present invention can be in the form of conventional emulsifiable concentrates, or emulsifiable concentrates in water-soluble film bags which eliminates concerns about container disposal and/or recycle, or they can be in the form of water-dispersible dry flowables.

Representative water-insoluble organic pesticides which can be employed in the practice of the present invention include one or more pesticides from the classes of acylurea insecticides, organophosphorous insecticides, pyrethroid insecticides, aryloxyaryl herbicides and sulfonamide herbicides. Examples of such pesticides include:

the acylurea insecticides described in U.S. Pat. Nos. 4,148,902; 4,173,637 and Reissue Pat. No. 30,563, which are incorporated herein by reference, and especially 1-[3,5-dichloro-4-((5-trifluoromethyl)-3-chloro-2-pyridyloxy)phenyl]-3-(2,6-difluorobenzoyl) urea (common name Chlorfluazuron);

the organophosphorous insecticides and acaricides described in U.S. Pat. Nos. 3,244,586; 4,429,125; 4,654,329 and 4,729,987 which are incorporated herein by reference, especially chlorpyrifos and chlorpyrifos-methyl;

the pyrethroid insecticides and miticides such as cypermethrin, permethrin and fenvalerate;

the aryloxyaryl herbicides described in U.S. Pat. Nos. 4,550,192; 4,551,170 and 4,750,931 which are incorporated herein by reference, especially 2-(4-(((5-trifluoromethyl)-2-pyridinyl)oxy)phenoxy)propanoic acid; 2-(4-((3-chloro-5-trifluoromethyl)-2-pyridinyl) oxy)phenoxy)propanoic acid methyl ester; 2-(4-((3-chloro-5-trifluoromethyl)-2-pyridinyl)-oxy)phenoxy) propanoic acid ethyl ester; and 2-(4-(((3-fluoro-5-trifluoromethyl)-2-pyridinyl)oxy)phenoxy) propanoic acid methyl ester; and the sulfonamide herbicides described in U.S. Pat. Nos. 4,731,446; 4,740,233; 4,741,764 and 4,755,212 which are incorporated herein by reference, especially N-(2,6-dichlorophenyl)-5,7-dimethoxy-1,2,4-triazolo (1,5a) pyrimidine-2-sulfonamide; N-(2,6-dichloro-3-methylphenyl)-5,7-dimethoxy-1,2,4-triazolo(1,5a) pyrimidine-2-sulfonamide; N-(2,6-dichlorophenyl)-5-methyl-7-methylthio-1,2,4-triazolo-(1,5a)pyrimidine-2-sulfonamide; N-(2-trifluoromethylphenyl)-5-methyl-7-methylthio-1,2,4-triazolo-(1,5a)pyrimidine-2-sulfonamide; N-(2,6-dichloro-3-methylphenyl)-7-methoxy-5-methyl-1,2,4-triazolo(1,5a)pyrimidine-2-sulfonamide; and N-(2,6-dichloro-3-methylphenyl)-7-ethoxy-5-methyl-1,2,4-triazolo(1,5a) pyrimidine-2-sulfonamide.

the acetanilides and chloroacetanilide herbicides, such as, alachlor;

the dinitroaniline herbicides, such as, trifluralin and ethafluralin;

the thiocarbamates, such as, EPTC and triallate;

the isoxazolidinone herbicides, such as, clomazone;

the pyridinemethanols, such as, fenarimol.

Other representative water-insoluble organic agricultural pesticides useful in the practice of this invention include:

amide insecticides, benzonitrile herbicides, benzofuranyl methanesulphonate herbicides, carbamate herbicides, hydroxy cyclohexanone herbicides, imidazolinone herbicides, triazine herbicides, and triazinone herbicides; alanine methyl ester fungicides and pyrimidinemethanol fungicides; benzene acetate insecticides, cyclic sulfite insecticide and acaricides, diphenyl chloride insecticides and glycine ester insecticides.

Examples of many other such pesticides are listed in the *Pesticide Dictionary*, 1992 Farm Chemicals Handbook, Meister Publishing Company.

The substantially non-aqueous formulation compositions can comprise blends of surfactants with a hydrophilic-lipophilic balance (HLB) range of 10 to 20, and compatibilizing agents which include organic solvents compatible with the copolymer and defined by a solubility parameter range of about 9 to about 15 $(cal/cm^3)^{0.5}$. The HLB number value for various surfactants is listed by W. C. Griffin, in *Kirk-Othmer Encyclopedia of Chemical Technology*, 3rd ed. (M. Grayson, ed.), Vol. 8, Wiley-Interscience, New York, 1979, pages 900–930. The solubility parameter value for various solvents is listed by H. Burrell, in *Polymer Handbook*, Second ed. (J. Brandrup, E. H. Immergut, ed.), Wiley Interscience, New York, 1975, IV–337, Tables 1 and 2, pp. 341–348.

A non-ionic surfactant solution of the amphipathic graft copolymer composition can be readily mixed with the water-insoluble organic pesticide material, including an organic solvent, if the organic pesticide is a solid, to form a dilutable substantially non-aqueous formulation that can be easily diluted with water. A stable aqueous emulsion results that is non-settling and is freeze-thaw stable, i.e., capable of reconstitution after freeze-thaw cycling. In addition, small oil-in-water emulsion particles, measuring less than 5000 Å and preferably less than 1500 Å in size, are formed by simple low shear mixing upon dilution.

Certain of the water-insoluble organic pesticides set forth hereinabove which have high vapor pressures, when employed in formulations using conventional volatile solvents, are subject to high vaporization rates in certain applications due to both the compound's vapor pressure and the volatility of the solvents. These conventional formulations which employ volatile solvents as the compatibilizing agent thus have limited usefulness in treating situations where conservation tillage, reduced till or no-till practices are employed. In these practices, the pesticide formulation is applied onto the surface of the soil without immediate incorporation into the soil or where the formulation is applied onto the surface of the plants being treated. The above-indicated high vaporization problems can be overcome by modifying the formulation to reduce the amount of high vapor pressure volatile solvents present and also include using low vapor pressure inert plasticizer/oligomer materials which can also act as compatibilizing agents. The modified formulations contain the water-insoluble organic pesticides in admixture with the low vapor pressure inert plasticizers/oligomers and the amphipathic graft copolymer set forth above and while the modified formulations are useful with conventional soil incorporation practices, they are especially useful in the no-till practices outlined above.

The plasticizers/oligomers useful in preparing the above-modified formulations have low vapor pressure and have a loss by volatility in polyvinyl chloride of below about 20 weight percent as measured by ASTM D 1203-67. Representative plasticizers/oligomers include among others, those taught in the *Encyclopedia of Polymer Science and Engineering*, Supplement Vol., J. Wiley and Sons, New York, 1988, Table 3, pages 599–600, and in the 1992 "List Of Pesticide Product Inert Ingredients" set forth by the Office of Prevention, Pesticides and Toxic Substances of the U. S. Environmental Protection Agency, Washington, D.C. Such plasticizers/oligomers include:

abietic acid, 2,6-bis(1-methylheptadecyl)-p-cresol; abietic acid, diethylene glycol ester (CAS No. 10107-99-0); bis(2-ethylhexyl) azelate (CAS No. 103-24-2); bisphenol A/epichlorohydrin condensate (CAS No. 25068-38-6); butyl benzyl phthalate (CAS No. 85-68-7); butyl stearate (CAS No. 123-95-5); butyl naphthalene (CAS No. 31711-50-9); carboxypolymethylene resin (CAS No. 9007-20-9); castor oil (CAS No. 8001-79-4); epoxidized castor oil (CAS No. 105839-17-6); ethoxylated castor oil (CAS No. 61791-12-6); hydrogenated castor oil (CAS No. 8001-78-3); hydrogenated, ethoxylated castor oil (CAS No. 61788-85-0); oxidized castor oil (CAS No. 68187-84-8); cellulose (CAS No. 9004-34-6); cellulose acetate butyrate (CAS No. 9004-32-4); diisobutyl adipate (CAS No. 141-04-8); diisopropyl adipate (CAS No. 6938-94-9); diisononylphthalate (CAS No. 28553-12-0); diisooctyl maleate (CAS No. 1330-76-3); diisodecyl adipate (CAS No. 26761-40-0); dilauryl thiodipropionate (CAS No. 123-28-4); dioctyl maleate (CAS No. 2915-53-9); dioctyl phthalate (CAS No. 117-84-0); diphenyl ether (CAS No. 101-84-8); dipropylene glycol dibenzoate (CAS No. 27138-31-4); epoxidized linseed oil (CAS No. 8016-11-3); epoxidized soybean oil (CAS No. 8013-07-8); 2-ethylhexyl 12-hydroxystearate (CAS No. 29710-25-6); heptyl nonyl adipate; tricresyl phosphate; and wood rosin, an extract of pine stumps, composed of resin acids of the abetic and pimaric types having a phenanthrene nucleus as disclosed in the *Encyclopedia of Polymer Science and Engineering*, Vol. 14, J. Wiley and Sons, New York, 1988, pages 438–443.

The invention of the present application is further illustrated by the following examples wherein all parts are by weight.

EXAMPLE I

Preparation of a non-ionic surfactant solution of an anionic amphipathic graft copolymer composition.
Stage 1—Hydrophobic Solution Polymerization
A mixture of:

115.7 parts Tergitol™NP-7 (nonylphenol ethoxylate containing 7 moles of ethylene oxide purchased from Union Carbide), 23.3 parts of styrene, 23.3 parts of 2-ethylhexyl acrylate, 3.33 parts of glycidyl methacrylate, and 1.54 parts of VAZO™64 (2,2'-Azobis (2-methylpropanenitrile))

is heated to 80° C. in a stirred glass reactor and blanketed with an inert atmosphere of nitrogen. A mixture of 0.280 parts of 2-mercaptoethanol in 4.00 parts NP-7 is then added to the reactor in 0.5 part aliquots every 15 minutes after which the reaction is allowed to continue an additional hour at a temperature of about 80° C.
Stage 2—Hydrophilbic Monomer Polymerization
145.3 parts of NP-7 is added to the reactor in the Stage 1 product mixture and the following feed solution is continuously and proportionately added over two hours to the stirred reaction mixture at about 80° C.:
A mixture of 25.0 parts of 2-acrylamido-2-methylpropanesulfonic acid admixed with 20.0 parts of deionized (DI) water, 3.75 parts of dimethylaminoethyl methacrylate, 21.3 parts of methyl methacrylate, 0.14 part of t-butyl hydroperoxide admixed with 6.0 parts of DI water, 0.80 parts of sodium formaldehyde sulfoxylate admixed with 6.0 parts of DI water, and 0.28 parts of 2-mercaptoethanol admixed with 6.0 parts of DI water.

The reactor contents are maintained at 80° C. for an additional two hours.

The resulting non-ionic surfactant solution of an anionic amphipathic graft copolymer composition containing about 10 weight percent water and about 65 weight percent non-ionic surfactant, is clear and viscous at room temperature. The viscosity measures about 15,000 cps using a Gardner Bubble Viscometer.

EXAMPLE II

Preparation of a non-ionic surfactant solution of a cationic amphipathic graft copolymer composition.
Stage 1—Hydrophobic Solution Polymerization
A mixture of:

113.4 parts of Tergitol™NP-7 and 2.63 parts of tert-butyl peroctoate is heated to 90° C. in a stirred glass reactor and blanketed with an inert atmosphere of nitrogen.

A mixture of 41.3 parts of styrene, 41.2 parts of 2-ethylhexyl acrylate, 5.00 parts of glycidyl methacrylate, and 2.63 parts of tert-butyl peroctoate, as a separate feed, are added continuously and proportionately to the reactor over 1.5 hours.
Stage 2—Hydrophilbic Monomer Polymerization
The following reactants are added continuously and proportionately to the reactor over 1.5 hours:

12.5 parts of dimethylaminoethyl methacrylate, 0.10 parts of 2-mercaptoethanol, 2.25 parts of DI water, and 178.9 parts of Tergitol™NP-7

The reactor contents were maintained at 90° C. for an additional 2 hours. The reaction mixture is cooled to about 35° C. and 11.3 parts of iodomethane were added over 1 hour while increasing the temperature from 35° C. to 40° C., and maintaining the reaction mixture at that temperature for another 3.5 hours.

The resulting non-ionic surfactant/cationic amphipathic graft copolymer solution, with about 0.6 weight percent water and about 71 weight percent non-ionic surfactant, is clear, amber in color, and very viscous at room temperature. The viscosity measures about 100,000 cps.

EXAMPLE III

Preparation of a non-ionic surfactant solution of an anionic amphipathic graft copolymer composition.
Stage 1—Hydrophobic Solution Polymerization
A mixture of:

793.8 parts Tergitol™NP-7 and 18.4 parts tert-butyl peroctoate are heated to 90° C. in a stirred glass reactor and blanketed with an inert atmosphere of nitrogen.

A mixture of 433.1 parts styrene, 144.4 parts 2-ethylhexyl acrylate, 35.0 parts glycidyl methacrylate and a separate feed of 18.4 parts tert-butyl peroctoate were added proportionately to the reactor over 1.5 hours. During this addition period the reaction temperature reached a maximum temperature of 99° C.

Stage 2—Hydrophilbic Monomer Polymerization

The following feed solutions were added continuously and proportionately to the reactor over 1.5 hours with reaction temperature decreasing from 99° C. to 92° C.:

87.5 parts 2-acrylamido-2-methylpropane sulfonic acid admixed with 87.5 parts DI water, 41.0 parts dibutyl amine, 1176.7 parts Tergitol™NP-7, 0.7 parts 2-mercaptoethanol admixed with 15.8 parts DI water and the reactor contents maintained for an additional 2 hours at 90° C.

The polymer/non-ionic/water reaction mixture was transferred to a steam still and the residual monomers removed with the aid of a vacuum. The resulting amphipathic graft copolymer has a number average molecular weight of 15,000.

EXAMPLE IV

Preparation of a non-ionic surfactant solution of an anionic amphipathic graft copolymer composition.

Stage 1—Hydrophobic Solution Polymerization A mixture of:

113.4 parts Neodol (Reg. TM of the Shell Chemical Co.) 23-6.5 (linear primary alcohols in the $C_{12}$ to $C_{13}$ carbon number range with an average of 6.5 moles of ethylene oxide) and 2.63 parts tert-butyl peroctoate is heated to 90° C. in a stirred glass reactor and blanketed with an inert atmosphere of nitrogen.

A mixture of 27.5 parts styrene, 55.0 parts 2-ethylhexyl acrylate, 5.00 parts glycidyl methacrylate, and 2.63 parts tert-butyl peroctoate (by a separate feed line), were then added proportionately to the reactor over 1.5 hours.

Stage 2—Hydrophilbic Monomer Polymerization

After a period of ½ hour, a monomer solution consisting of:

12.5 parts 2-acrylamido-2-methylpropane sulfonic acid admixed with 12.5 parts DI water, and 5.85 parts dibutyl amine is added to the reactor continuously over 1.5 hours.

A solution of 0.10 part 2-mercaptoethanol, 2.25 DI water, and 168.1 parts Neodol™ 23-6.5 was then added continuously and proportionately over the last hour of the addition and the reactor contents are maintained for an additional 2 hours at 90° C.

EXAMPLE V

Preparation of a non-ionic surfactant solution of an amphipathic graft copolymer composition.

Stage 1—Hydrophobic Solution Polymerization

A mixture of:

272.0 parts Neodol™ (from the Shell Chemical Co) 45-7 (linear primary alcohols in the $C_{14}$ to $C_{15}$ carbon number range with an average of 7 moles of ethylene oxide), and 3.00 parts VAZO (Reg. TM) 64 (2,2'-Azobis (2-methylpropanenitrile))

is heated to 80° C. in a stirred glass reactor and blanketed with an inert atmosphere of nitrogen.

A mixture of 35.0 parts styrene, 35.0 parts 2-ethylhexyl acrylate, and 5.00 parts glycidyl methacrylate is added continuously over 1.5 hours to the stirred reaction mixture.

Stage 2—Hydrophilbic Monomer Polymerization

The following feed solutions are continuously and proportionately added over 1.5 hours to the stirred reaction mixture at about 80° C.:

To the reaction mixture was then added 25.0 parts 2-acrylamido-2-methylpropane sulfonic acid, 25.0 parts DI water, 0.10 parts 2-mercaptoethanol plus 4.5 parts DI water and the reactor contents are maintained at 80° C. for an additional two hours.

Numerous water-insoluble organic pesticides are easily formulated with solutions of non-ionic surfactants and the amphipathic graft copolymers of the present invention to form dilutable substantially non-aqueous emulsifiable concentrate compositions. These concentrates are formulated so as to provide the normal conventional content of the active pesticides in the diluted formulation for field use.

In general, the concentration of the active pesticides in the concentrate composition is from about 5.0 to about 95 percent by weight. In the final diluted formulation, the concentration of the active pesticides can be from about 0.001 to 50 percent by weight.

Agricultural emulsifiable concentrates are especially useful where the active ingredient (A.I.), if a low melting solid (m.p.<=100° C.), is premixed with a low vapor pressure inert plasticizer/oligomer or an organic solvent to form a fluid phase at or below ambient temperatures. This liquid phase is then mixed with the amphipathic graft copolymer composition, non-ionic surfactant, and minimal water to form a dilutable substantially non-aqueous formulation that is freeze-thaw stable. When the formulation is diluted with water, a diluted formulation of oil-in-water small emulsion particles readily forms with minimal mixing.

Preferred dilutable substantially non-aqueous agricultural formulations contain the following components:

(1) amphipathic graft copolymer, (2) water-insoluble organic pesticide, (3) low vapor pressure inert plasticizer-/oligomer materials and/or a water-insoluble organic solvent and/or crystal growth preventor for the pesticide to maintain a liquid state and to allow the formulation to reconstitute after freeze-thaw cycles, (4) a non-ionic surfactant, (5) additives such as neutralents, color and odor-masking agents, hydrotopes, electropes, freeze-thaw agents and anti-foam agents and (6) less than 10 percent by weight of water.

The ratio of oil, which includes pesticide plus solvent, to non-ionic surfactant ranges from about 1.5:1 to 3:1 for minimum particle size of the diluted substantially non-aqueous formulation diluted to a 2 percent active in water dilution.

The preferred minimum particle size of the diluted oil-in-water emulsion occurs when the amphipathic graft copolymer is present in the concentrate composition in the range of from about 7 to 10 weight percent. The range of the charge density, expressed as milliequivalents of ionizable charge per gram polymer, is surprisingly broad and is from about 0.5 meq/g to 1.5 meq/g.

The water level is generally less than about 10 weight percent for the dilutable non-aqueous concentrate formulation.

EXAMPLE VI
Freeze-thaw test:

The freeze-thaw cycling test is conducted by cooling about 20 grams of a sample of the formulation to be tested at −10° C. to −15° C. until it solidifies, which usually takes about 2 hours. The sample is then allowed to thaw and equilibrate at room temperature overnight, without agitation or additional heat. Observed crystal residue, phase separation, or both, result in a test failure. The procedure is repeated two or three times and if the formulation reconstitutes under these conditions, it is rated as passing.

EXAMPLE VII
Thermal fluctuation test:

The thermal fluctuation test is conducted by heating about 20 grams of a sample of the non-aqueous concentrate to be tested at about 50° C. The concentrate is observed for changes with time, such as, color, clarity, gel formation and phase separation. Aliquots are removed weekly and allowed to cool to room temperature. The aliquot is diluted to a 2 weight percent active in water before observing dilution characteristics, such as ease of dilution, particle size and the rate of settling. The test is performed over a maximum 3 month period with noted changes upon storage and dilution of the test concentrate.

In order for the hydrophobic/hydrophilic copolymer to function as a stabilizer for pesticide formulations when diluted, the copolymer should be gel free. This is accomplished by adjusting the initiator and chain transfer agent levels in both hydrophobic and hydrophilic polymerizations. This technique allows for preparation of dilutable substantially non-aqueous concentrate formulation compositions without removal of water and features high concentrations of the active pesticide. Diluted formulations of these concentrates with water form stable oil-in-water emulsions having particle sizes of less than 5000 Å. The resulting dilutable substantially non-aqueous formulations with the amphipathic graft copolymer compositions of the present invention are more stable to stress (freeze/thaw and thermal fluctuations during storage) than formulations made employing conventional or known polymeric surfactants and conventional or structured particle latexes as the carriers or stabilizers.

The preferred formulations of the present invention contain the anionic amphipathic graft copolymer stabilizers in non-ionic surfactant solutions selected to optimize stability of the concentrate and its dilution in water while minimizing emulsion particle size. Preferred amphipathic graft copolymer stabilizers are obtained by using a combination of non-ionic hydrophobic vinyl monomers and a graftable vinyl monomer and a pH independent anionic vinyl monomer. The non-ionic hydrophobic monomers are selected on the basis of aliphatic and aromatic balance required by the non-ionic surfactant and the oil phase which is a solution of the water-insoluble organic pesticide material plus low vapor pressure inert plasticizer/oligomer or an organic solvent or crystal growth preventor. The preferred monomers are styrene for aromaticity and 2-ethylhexyl acrylate for aliphatic character. The preferred graftable monomer is glycidyl methacrylate. The preferred pH independent anionic monomer is 2-acrylamido-2-methylpropanesulfonic acid ((AMPS)™ from Lubrizol).

The preferred non-ionic surfactants are ethoxylate adducts of alkylphenols or alcohols having a hydrophile-lipophile balance value (HLB) in the range of 10 to 13 and the most preferred range of 11.5 to 12.5 for minimum particle size of the dilute oil-in-water pesticide emulsion. Preferred non-ionic surfactants for minimum particle size and stability are ethoxylated nonylphenols where the average number of moles of ethylene oxide ranges from 5 to 9. These polymer and non-ionic choices are dependent on the specific characteristics of the oil phase. The non-ionic surfactants are present in the concentrate formulation in an amount of from about 10.0 to about 50.0 weight percent of the total formulation.

Water-insoluble organic solvents or plasticizers of low volatility are also useful in preparing the dilutable substantially non-aqueous formulations. They are used to form liquid solutions with the pesticides to form an oil phase that remains noncrystalline for optimum low temperature stability and reconstitution of formulations after freeze-thaw cycling.

It is desirable for the solvent/plasticizer to be water-insoluble and compatible with the pesticide, the hydrophobic component of the amphipathic graft copolymer, and the hydrophobic component of the non-ionic surfactant. This gives desirable small particle size oil-in-water dilutions with excellent stability and movement in the soil, especially if the copolymer is anionic.

Solvents/crystal growth preventors or plasticizers of choice include one or more of methyl esters of fatty acids such as caproic, lauric, myristic, oleic and tall oil; glycerides such as the oils of cottonseed, soybean, castor bean, and corn; triacetin; tributyl citrate; polyglycols; N-alkylated pyrrolidones such as the methyl, octyl and dodecyl alkyl derivatives; and terpenes such as d-limonene. Preferred solvents/crystal growth preventors or plasticizers are one or more of the methyl esters of lauric, myristic, oleic acids and the N-alkylated pyrrolidones with methyl and octyl being the preferred alkyl groups. The solvents/crystal growth preventors or plasticizers are present in an amount of from about 0 to about 300 weight percent based on the water-insoluble organic pesticide.

Formulations providing for improved controlled leaching, release, and volatility can be designed using variables of hydrophobic/hydrophilic, aromatic/aliphatic character of the hydrophobic polymer portion and charge type/level of the hydrophilic polymer portion in the amphipathic graft copolymer compositions of this invention in the presence of formulation additives comprising plasticizers/oligomers, water-insoluble solvents, neutralents, color and odor-masking agents, hydrotopes, electropes, freeze-thaw agents, anti-foam agents and monomeric ionic surfactants.

EXAMPLE VIII
Preparation of a dilutable substantially non-aqueous concentrate formulations Separate dilutable concentrate formulations are shown in Table I. These are prepared by employing one or more of the following pesticides[1]: alachlor, chlorpyrifos, chlorpyrifos-methyl, triallate, and trifluralin in admixture with the amphipathic graft copolymer compositions[3] of Example III.

TABLE I

Dilutable Substantially Non-aqueous Concentrate Formulations

| Concentrate Formulation Components | Weight percent |
| --- | --- |
| Water-insoluble organic pesticide (1) | 40.0 |
| Solvent: Methyl Laurate | 26.0 |
| Non-ionic Surfactant: Tergitol ™ NP-7- (2) | 22.0 |
| Amphipathic graft copolymer composition(3) | 8.0 |
| Water | 4.0 |
| Total | 100.0 |

(1) see above.
(2) Tergitol ™ NP-7 (Reg. TM) (nonylphenol with an average of 7 moles of ethylene oxide from Union Carbide).
(3) see above.

EXAMPLE IX

Preparation of a diluted formulation.

A dilutable substantially non-aqueous formulation is diluted with water to reduce the water-insoluble material content for proper activity and ease of application as shown below in Table II.

TABLE II

Diluted Formulation from Concentrate

| Formulation Components | Weight percent |
| --- | --- |
| 40 percent Chlorpyrifos Concentrate Formulation prepared as in Example IX | 5.0 |
| Water | 95.0 |
| Total | 100.0 |

This diluted formulation has small oil-in-water particle sizes of about 900 Å when diluted with water, using chlorpyrifos as an insecticide at (40.0 percent by weight), methyl laurate (26 percent by weight), Tergitol™ NP-7 (22 percent by weight), amphipathic ionic copolymeric carrier (8 percent by weight) and water (4 percent by weight).

EXAMPLE X

Another aqueous formulation is prepared by simply mixing the following: fenarimol fungicide (30.0 percent by weight), methyl pyrrolidone (30.0 percent by weight), Tergitol™ NP-7 non-ionic surfactant (31.1 percent by weight), amphipathic graft copolymer composition (8.0 percent by weight), and water (0.9 percent by weight). The particle size upon dilution with water measures about 1140 Å.

EXAMPLE XI

One example of a useful anionic dilutable substantially non-aqueous formulation is prepared by simply mixing a solution of a low melting agricultural pesticide, e.g., chlorpyrifos and methyl laurate, with the non-ionic surfactant/ amphipathic anionic copolymer/water solution in the following weight ratio: 42/26/21/8/3. This formulation has excellent reconstitution after freeze-thaw cycling.

EXAMPLE XII

A useful cationic dilutable substantially non-aqueous formulation is prepared by simple mixing. The formulation comprises 42 parts of chlorpyrifos, 25 parts of methyl laurate and 33 parts of a solution of Tergitol™ NP-7/ amphipathic cationic copolymer/water in the following weight ratio: 42/25/23.5/9.3/0.2. An aqueous dilution of this formulation forms a diluted formulation with oil-in-water emulsion particles that are substantive to negatively charged substrates.

EXAMPLE XIII

A dilutable substantially non-aqueous concentrate formulation is prepared by simply mixing the low water content amphipathic graft copolymer/non-ionic surfactant mixture with chlorpyrifos plus the methyl ester of lauric acid as a solvent. The formulation composition is 42 percent chlorpyrifos, 25 percent methyl laurate and 33 percent of a solution of Tergitol™ NP-7, amphipathic graft copolymer and water in the following weight ratio: 42/25/21.7/8.6/2.7. The density of this clear solution measures 1.13 g/mL. This oil based formulation is placed in a bag or container composed of partially hydrolyzed polyvinyl acetate. When the bag is added to water in a tank, the bag dissolves and the concentrate formulation contained therein mixes easily in the water to form a ready-to-use stable oil-in-water emulsion. The incorporation of the bag into the water has little effect on the resulting emulsion particle size. Table III which follows, compares the emulsion particle size in the diluted formulation as a function of the level of polymer in the film wall of the bag.

TABLE III

PARTICLE SIZE OF DILUTED FORMULATION FROM A CONTAINERIZED DILUTABLE SUBSTANTIALLY NON-AQUEOUS EMULSIFIABLE CONCENTRATE

| Parts by weight of 2 mil film(1) per 100 parts of diluted formulation | Emulsion particle size in Angstroms(2) |
| --- | --- |
| 0 | 1100 |
| 0.85 | 1100 |
| 1.7 | 1140 |
| 2.5 | 1140 |

(1) Packaging ratio of surface to volume = 1.45.
(2) Dilution of oil based 42 weight percent chlorpyrifos formulation contained with and without film bags to 2 weight percent chlorpyrifos in water. Emulsion particle size measured by Brice Phoenix Light Scattering Unit.

EXAMPLE XIV

Preparation of a non-ionic surfactant solution of an anionic amphipathic graft copolymer composition. By following the above set forth preparative procedures, a copolymer containing 25 weight percent 2-acrylamido-2-methylpropanesulfonic acid (AMPS), 37.5 weight percent n-butyl methacrylate and 37.5 weight percent 2-ethylhexyl acrylate prepared by reacting the above ingredients and tert-butyl peroctoate in Tergitol™ NP-7.

EXAMPLE XV

Preparation of a dilutable substantially non-aqueous concentrate low volatilization formulations as set forth in TABLE IV.

TABLE IV

Dilutable Substantially Non-aqueous Concentrate Formulations

| Concentrate Formulation Components | Weight percent |
|---|---|
| Organic pesticide: Trifluralin | 33.0 |
| Plasticizer: Butyl benzyl phthalate | 33.0 |
| Non-ionic Surfactant: Tergitol NP-7(1) | 24.8 |
| Amphipathic graft copolymer composition(2) | 9.2 |
| total | 100.0 |

(1)Tergitol NP-7 (Reg. TM) (nonylphenol with an average of 7 moles of ethylene oxide from Union Carbide).
(2)Amphipathic graft copolymer compositions of Example XV.

EXAMPLE XVI

Preparation of a non-ionic surfactant solution of an anionic amphipathic graft copolymer composition. By following the above set forth preparative procedures, a copolymer containing 37.3 weight percent styrene, 37.3 weight percent n-butyl methacrylate, 2.7 weight percent glycidyl methacrylate and 22.6 weight percent 2-acrylamido-2-methylpropanesulfonic acid (AMPS) prepared by reacting the above ingredients and tert-butyl peroctoate in Tergitol™ NP-7.

EXAMPLE XVII

Preparation of a dilutable substantially non-aqueous concentrate low volatilization formulations as set forth in TABLE V.

TABLE V

Dilutable Substantially Non-aqueous Concentrate Formulations

| Concentrate Formulation Components | Weight percent |
|---|---|
| Organic pesticide: Trifluralin | 33.0 |
| Plasticizer: Butyl benzyl phthalate | 16.5 |
| Oligomer: wood rosin(1) | 16.5 |
| Non-ionic Surfactant: Tergitol NP-7(2) | 24.8 |
| Amphipathic graft copolymer composition(3) | 9.2 |
| total | 100.0 |

(1)wood rosin (a proprietary product of Sovereign Chemical Co., which is an extract of pine stumps, composed of resin acids of the abetic and pimaric types having a phenanthrene nucleus.
(2)Tergitol NP-7 (Reg. TM) (nonylphenol with an average of 7 moles of ethylene oxide from Union Carbide).
(3)Amphipathic graft copolymer compositions of Example XVI.

EXAMPLE XVIII
Pesticide Activity

The organic pesticides employed in the stable aqueous emulsion formulations of the water-insoluble organic pesticide/surfactant-amphipathic graft copolymer mixtures of the present invention have all been found to maintain their basic biological activity in the formulations of the instant invention as compared to the basic biological activity of the pesticides when the pesticide is used in conventional formulations.

EXAMPLE XIX

Representative formulations of the present invention were evaluated to determine their effectiveness in preemergent operations.

Water dispersions were prepared by mixing the following materials with water.

Concentrate Formulation

| Formulation Components | Weight percent |
|---|---|
| Trifluralin | 35.00 |
| Amphipathic graft copolymer reaction product mixture of Example III | 8.80(a) |
| Tergitol™ NP-7 | 24.04 |
| Methyl Laurate | 31.00 |
| Dibutyl amine | 0.16 |
| Water | 1.00 |
| Total | 100.00 |

(a)= amount is the weight of copolymer only

Seed beds of a loamy sand field soil of good nutrient content were prepared in 1.0×2.0 foot plastic trays about 2–3 inches deep. The soil was seeded with seeds of giant foxtail (*Setaria faberi*) at a planting rate of about 100 seeds per bed. The seeds were covered with soil to a depth of ¼ to ½ inch. The beds were watered with a predetermined amount of water followed by the application, by a moving spray, of a 0.24 percent emulsion of a diluted formulation prepared by diluting the above concentrate formulation with a predetermined amount of water. Other beds were left untreated to serve as controls. After treatment, the beds were maintained for 21 days under greenhouse conditions for good plant growth. At the end of this period, the beds were examined to determine the amount of kill and control of giant foxtail. It was determined that 78 percent preemergent control was obtained.

Various modifications may be made in the present invention without departing from the spirit or scope thereof as will be apparent to those skilled in the art.

We claim:

1. A non-latex, water dilutable substantially non-aqueous agricultural pesticide concentrate formulation containing less than 15 percent water which is non-settling and Freeze-thaw stable which comprises a hydrophobic solution polmerized amphipathic graft copolymer having a charge density of from about 0.5 to about 1.5 meq/gram polymer and a number average molecular weight of between about 5,000 and about 250,000, which consist of a hydrophobic backbone copolymer prepared from at least two ethylenically unsaturated hydrophobic monomers, said hydrophobic backbone copolymer containing graftable, reactive functional groups to which is in-chain grafted a arnphipathic copolymer prepared from at least one ethylenically unsaturated hydrophilic monomer containing stabilizing pH independent ionic groups, a water-insoluble organic agricultural pesticide, a compatibilizing agent for the pesticide and a non-ionic surfactant, said formulation when diluted in water forms an oil-in-water emulsion wherein the particle sizes of said emulsion are less than 5000 Å.

2. A formulation as defined in claim 1 wherein the water-insoluble organic agricultural pesticide is a member of the group consisting of alachlor, chlorpyrifos, chlorpyrifos-methyl, fenarimol, triallate, and trifluralin.

3. A formulation as defined in claim 1 comprising up to about 65 weight percent pesticide and less than about 6 weight percent water.

4. A formulation as defined in claim 1 which also contains at least one formulation additive of the group consisting of neutralents, color and odor-masking agents, freeze-thaw agents and antifoam agents.

5. A formulation as defined in claim 1 wherein the compatibilizing agent for the water-insoluble organic pesticide is an organic solvent.

6. A formulation as defined in claim 1 wherein the organic solvent is an ester of a fatty acid.

7. A formulation as defined in claim 1 wherein the compatibilizing agent for the water-insoluble organic pesticide is a plasticizers/oligomer material.

8. A water-diluted agricultural pesticide formulation which comprises a mixture of a non-latex water dilutable substantially non-aqueous agricultural pesticide concentrate formulation containing less than 15 percent water which is non-settling and freeze-thaw stable which comprises a hydrophobic solution polymerized amphipathic graft copolymer having a charge density of from about 0.5 to about 1.5 meq/gram polymer and a number average molecular weight of between about 5,000 and about 250,000, which consist of a hydrophobic backbone copolymer prepared from at least two ethylenically unsaturated hydrophobic monomers, said hydrophobic backbone copolymer containing graftable, reactive functional groups to which is in-chain grafted an amphipathic copolymer prepared from at least one ethylenically unsaturated hydrophilic monomer containing stabilizing pH independent ionic groups, a water-insoluble organic agricultural pesticide, a compatibilizing agent for the pesticide, a non-ionic surfactant and water, said water diluted formulation being non-settling and freeze-thaw stable and wherein the particle sizes of the thus formed oil-in-water emulsion are less than 5000 Å.

9. A water-diluted formulation as defined in claim 8 wherein the water-insoluble organic agricultural pesticide is a member of the group consisting of alachlor, chlorpyrifos, chlorpyrifos-methyl, fenarimol, triallate, and trifluralin.

10. A water-diluted formulation as defined in claim 8 which also contains at least one formulation additive of the group consisting of neutralents, color and odor-masking agents, freeze-thaw agents and antifoam agents.

11. A water-diluted formulation as defined in claim 8 wherein the compatibilizing agent for the water-insoluble organic pesticide is an organic solvent.

12. A water-diluted formulation as defined in claim 11 wherein the solvent for a water-insoluble pesticide is an ester of a fatty acid.

13. A water-diluted formulation as defined in claim 8 wherein the compatibilizing agent for the water-insoluble organic pesticide is a plasticizers/oligomer material.

14. A method for the control of the growth of agricultural pests in foliar and soil environments which comprises contacting said pests and their foliar and soil environments with a pesticidally effective amount of an aqueous formulation which comprises a mixture of water and a water-insoluble organic pesticide with a compatibilizing agent for the pesticide, in admixture with a non-latex water dilutable substantially non-aqueous agricultural pesticide concentrate formulation containing less than 15 percent water which is non-settling and freeze-thaw stable and wherein the particle sizes of the thus formed oil-in-water emulsion are less than 5000 Å which comprises a hydrophobic solution polymerized amphipathic graft copolymer having a charge density of from about 0.5 to about 1.5 meq/gram polymer and a number average molecular weight of between about 5,000 and about 250,000, which consist of a hydrophobic backbone copolymer prepared from at least two ethylenically unsaturated hydrophobic monomers, said hydrophobic backbone copolymer containing graftable, reactive functional groups to which is in-chain grafted an amphipathic copolymer prepared from at least one ethylenically unsaturated hydrophilic monomer containing stabilizing pH independent ionic groups, and a non-ionic surfactant.

15. A method as defined in claim 14 wherein the water-insoluble organic pesticide is a member of the group consisting of alachlor, chlorpyrifos, chlorpyrifos-methyl, fenarimol, triallate, and trifluralin.

16. A method as defined in claim 14 wherein the compatibilizing agent for the water-insoluble organic pesticide is an organic solvent.

17. A water-diluted formulation as defined in claim 16 wherein the solvent for a water-insoluble pesticide is an ester of a fatty acid.

18. A method as defined in claim 14 wherein the compatibilizing agent for the water-insoluble organic pesticide is a plasticizers/oligomer material.

* * * * *